United States Patent
Flugge-Berendes et al.

(10) Patent No.: US 8,039,011 B2
(45) Date of Patent: Oct. 18, 2011

(54) SKIN COOLING COMPOSITIONS

(75) Inventors: Lisa Ann Flugge-Berendes, Appleton, WI (US); Scott W. Wenzel, Neenah, WI (US); Corey T. Cunningham, Larsen, WI (US); Pierre R. Joseph, Appleton, WI (US); Benjamin J. Kruchoski, Appleton, WI (US); Thomas G. Shannon, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 885 days.

(21) Appl. No.: 11/545,409

(22) Filed: Oct. 10, 2006

(65) Prior Publication Data

US 2008/0085290 A1      Apr. 10, 2008

(51) Int. Cl.
*A61K 8/02*     (2006.01)
*A61K 31/745*   (2006.01)
*A61P 43/00*    (2006.01)

(52) U.S. Cl. .................. 424/401; 424/78.02; 424/78.03; 607/114

(58) Field of Classification Search .................. None
See application file for complete search history.

(56) References Cited

U.S. PATENT DOCUMENTS

| | | | |
|---|---|---|---|
| 6,207,738 B1 | 3/2001 | Zuckerman et al. | |
| 6,689,466 B2 | 2/2004 | Hartmann | |
| 2005/0013821 A1* | 1/2005 | Anton | 424/184.1 |
| 2005/0053632 A1 | 3/2005 | Schafer et al. | |
| 2009/0110656 A1* | 4/2009 | Lemke et al. | 424/78.02 |
| 2009/0157153 A1* | 6/2009 | Lemke et al. | 607/114 |

FOREIGN PATENT DOCUMENTS

| | | | |
|---|---|---|---|
| CN | 1233478 A | * | 11/1999 |
| CN | 1736402 A | * | 2/2006 |
| EP | 1 250 940 A1 | | 10/2002 |
| EP | 1 250 941 A1 | | 10/2002 |
| EP | 1 398 306 A2 | | 3/2004 |
| EP | 1 263 379 B1 | | 10/2004 |
| EP | 1 201 219 B1 | | 12/2005 |
| EP | 1 250 914 B1 | | 5/2006 |
| JP | 59193818 A | * | 11/1984 |
| JP | 2003253292 A | * | 9/2003 |
| RU | 2014823 C1 | * | 6/1994 |
| WO | WO 00/42983 A1 | | 7/2000 |
| WO | WO 00/62737 A1 | | 10/2000 |
| WO | WO 01/21146 A1 | | 3/2001 |
| WO | WO 01/60305 A1 | | 8/2001 |
| WO | WO 03/007908 A2 | | 1/2003 |
| WO | WO 03/007909 A2 | | 1/2003 |
| WO | WO 2006/131203 A1 | | 12/2006 |

OTHER PUBLICATIONS

Leffingwell, John C., "Cool Without Menthol & Cooler Than Menthol and Cooling Compounds as Insect Repellents," Internet web page "www.leffingwell.com/cooler_than_menthol.htm", First posted Dec. 11, 2001, updated Apr. 5, 2006, pp. 1-23.

Watson, H.R. et al., "New Compounds With the Menthol Cooling Effect," *Journal of the Society of Cosmetic Chemists*, vol. 29, 1978, pp. 185-200.

* cited by examiner

*Primary Examiner* — Chris R Tate
*Assistant Examiner* — Aaron Kosar
(74) *Attorney, Agent, or Firm* — Randall W. Fieldhack

(57) ABSTRACT

Provided is a temperature change composition including a neurosensory component; and a first phase change component having a first phase change temperature between about 15 degrees C. and about 40 degrees C. Also provided is a temperature change composition including an evaporative cooling component; and a first phase change component having a first phase change temperature. Also provided is a temperature change composition for cooling skin, the composition including a first phase change component having a first phase change temperature; and a second phase change component having a second phase change temperature different from the first phase change temperature.

29 Claims, No Drawings

SKIN COOLING COMPOSITIONS

BACKGROUND OF THE INVENTION

The invention relates to a skin cooling composition, and in particular to a skin cooling composition that provides short and long term skin cooling. There are a variety of products that are applied to the skin. It would be desirable under many circumstances if such products provided a cooling feeling to the skin when the products were applied to the skin. Some example products include lotions, creams, moisturizers, bath agents and insect-repellent sprays (among others).

Existing products typically provide skin cooling by combining skin cooling agents with other substances. However, many existing products fail to provide satisfactorily strong and long lasting skin cooling.

There are several different means to impart a cooling sensation to the skin, including using evaporation, neurosensory components, or physical agents such as phase change materials (PCMs). One example cooling agent is menthol which provides cooling in the form of a physiological or neurosensory effect on nerve endings in the human body that sense temperature. The cooling sensation from menthol is not due to latent heat of evaporation but appears to be the result of direct stimulus on the cold receptors at the nerve endings.

There is a need for skin cooling compositions that provide a refreshing feeling during or after use of the product. The skin cooling compositions should provide cooling strength and persistence while also being compatible with other agents that may be used in various skin products. Formulations that provide consistent, long-term cooling to the skin are desirable.

While particular aspects and/or individual features of the present invention have been illustrated and described, it would be obvious to those skilled in the art that various other changes and modifications can be made without departing from the spirit and scope of the invention. Further, it should be apparent that all combinations of such aspects and features are possible and can result in preferred executions of the invention.

SUMMARY OF THE INVENTION

There are disadvantages to the use of each of evaporation, neurosensory components, and physical agents such as phase change materials. Evaporation requires a substantially moist product or formulation that many people may not like. Neurosensory components are not felt by everyone and are fairly limited in their duration. Even encapsulated neurosensory components currently available lose effectiveness after about 20 to 30 minutes. Phase change materials tend to not give a dramatic temperature change.

A combination of two or more of these in the same formulation, including the use of neurosensory components in conjunction with phase change materials, give a longer-lasting sensation of cooling to a majority of users. In addition, the combination of phase change materials with different melting points extends the sensation of cooling.

The present invention relates to skin cooling compositions and methods for preparing skin cooling compositions. The skin cooling compositions provide immediate cooling of the skin as well as longer term cooling of the skin.

For example, in one aspect of the present invention, the invention includes a temperature change composition including a neurosensory component; and a first phase change component having a first phase change temperature between about 15 degrees C. and about 40 degrees C.

In another aspect of the present invention, the invention includes a temperature change composition including an evaporative cooling component, wherein the evaporative cooling component is one of a hydrocarbon, a short chain alcohol, a small branched chain alcohol, a fluorinated hydrocarbon, a fluorinated alcohol, a fluorinated ether, a low molecular weight grade of dimethicone, and a volatile cyclomethicone; and a first phase change component having a first phase change temperature between about 15 degrees C. and about 40 degrees C.

In another aspect of the present invention, the invention includes a temperature change composition for cooling skin, the composition including a first phase change component having a first phase change temperature; and a second phase change component having a second phase change temperature different from the first phase change temperature.

In another aspect of the present invention, the invention includes a temperature change composition including a neurosensory component; an evaporative cooling component, wherein the evaporative cooling component is one of a hydrocarbon, a short chain alcohol, a small branched chain alcohol, a fluorinated hydrocarbon, a fluorinated alcohol, a fluorinated ether, a low molecular weight grade of dimethicone, and a volatile cyclomethicone; and a first phase change component having a first phase change temperature between about 15 degrees C. and about 40 degrees C.

In another aspect of the present invention, the invention includes a temperature change composition including a neurosensory component; and an evaporative cooling component, wherein the evaporative cooling component is one of a hydrocarbon, a short chain alcohol, a small branched chain alcohol, a fluorinated hydrocarbon, a fluorinated alcohol, a fluorinated ether, a low molecular weight grade of dimethicone, and a volatile cyclomethicones.

DETAILED DESCRIPTION OF THE INVENTION

It is to be understood by one of ordinary skill in the art that the present discussion is a description of exemplary aspects of the present invention only, and is not intended as limiting the broader aspects of the present invention.

The invention relates to a skin cooling composition that provides short and long term skin cooling. The composition is readily applied to the skin. The composition may also be incorporated into many skin-related products such that the products provide a refreshing feeling on the skin of individuals who use the products. In addition, the composition may be readily mixed with many other materials that can be included in products that are applied to the skin.

The cooling composition of the present invention is made by adding to a base formulation at least two of first and second phase change materials, a neurosensory component, and an evaporative cooling component. The neurosensory component can be one such as menthol, menthol derivatives, or an encapsulated cooling agent such SALCOOL cooling composition from Salvona Technologies of New Jersey, U.S. In one example, the combination of a phase change material, which gives an immediate cooling sensation, and a neurosensory component, which is slower acting, allows for formulations that impart a cooling sensation over a longer period of time.

An exemplary formulation uses the base formulation for HUGGIES Shea Butter Lotion available from Kimberly-Clark Corp., with 10% phase change material such as LURA-PRET 28 phase change powder available from BASF in Ludwigshafen, Germany and 5% neurosensory component such as SALCOOL 4653 cooling composition from Salvona Technologies of New Jersey, U.S. Different amounts of the cooling agents can be used to generate the desired feel. In addition, different combinations of phase change material can be employed to expand the range of temperature where a cooling sensation is felt.

The cooling composition of the present invention also includes, by adding to the base formulation, a phase change material or a mixture of phase change materials.

In general, a phase change material includes any substance that has the capability of absorbing or releasing thermal energy to reduce or eliminate heat flow at or within a temperature stabilizing range. The temperature stabilizing range may include a particular transition temperature or range of transition temperatures. A phase change material used in conjunction with various aspects of the present invention preferably will be capable of altering a flow of thermal energy during a time when the phase change material is absorbing or releasing heat, typically as the phase change material undergoes a transition between two states (e.g., liquid and solid states, liquid and gaseous states, solid and gaseous states, or two solid states). This action is typically transient, meaning it will occur until a latent heat of the phase change material is absorbed or released during a heating or cooling process. Thermal energy may be stored or removed from the phase change material, and the phase change material typically can be effectively recharged by a source of heat or cold. For the purposes of the present invention, materials with transition or phase change temperatures between about 15 degrees C. and about 40 degrees C. are appropriate for use in cooling skin. In other embodiments of the present invention, materials may be chosen with transition temperatures between about 15 degrees C. and about 35 degrees C., between about 18 degrees C. and about 35 degrees C., between about 23 degrees C. and about 35 degrees C., between about 25 degrees C. and about 35 degrees C., between about 28 degrees C. and about 35 degrees C., or within any other suitable range.

Similarly, a mixture of phase change materials includes a mixture of transition temperatures. For example, the cooling sensation from the cooling composition may be extended by using a combination of phase change materials with different melting points. When the cooling composition is applied to the skin, the composition slowly warms to the temperature of the skin from room temperature. A phase change material will melt at its specified phase change temperature. That melting requires heat, which is taken from the skin, imparting a feeling of cooling. Once the material is melted, the cooling sensation dissipates. Having a range of phase change temperatures (melting points in this case) of the phase change materials would extend the range of temperatures where cooling is felt. In one example, a combination of phase change materials having phase change temperatures at 18° C., 28° C., and 35° C. would provide extended cooling to the skin as each phase change material in succession melts.

In various aspects of the present invention, the phase change material may be a solid/solid phase change material. A solid/solid phase change material is a type of phase change material that typically undergoes a transition between two solid states (e.g., a crystalline or mesocrystalline phase transformation) and hence typically does not become a liquid during use.

Suitable phase change materials of the present invention include, by way of example and not by limitation, LURAPRET phase change powder, a purified, encapsulated paraffin available from BASF, hydrocarbons (e.g., straight chain alkanes or paraffinic hydrocarbons, branched-chain alkanes, unsaturated hydrocarbons, halogenated hydrocarbons, and alicyclic hydrocarbons), waxes, oils, fatty acids, fatty acid esters, dibasic acids, dibasic esters, 1-halides, primary alcohols, aromatic compounds, anhydrides (e.g., stearic anhydride), ethylene carbonate, polyhydric alcohols (e.g., 2,2-dimethyl-1,3-propanediol, 2-hydroxymethyl-2-methyl-1,3-propanediol, ethylene glycol, polyethylene glycol, pentaerythritol, dipentaerythritol, pentaglycerine, tetramethylol ethane, neopentyl glycol, tetramethylol propane, monoaminopentaerythritol, diaminopentaerythritol, and tris (hydroxymethyl)acetic acid), polymers (e.g., polyethylene, polyethylene glycol, polypropylene, polypropylene glycol, polytetramethylene glycol, and copolymers, such as polyacrylate or poly(meth)acrylate with alkyl hydrocarbon side chain or with polyethylene glycol side chain and copolymers comprising polyethylene, polyethylene glycol, polypropylene, polypropylene glycol, or polytetramethylene glycol), and mixtures thereof.

A phase change material can be a mixture of two or more substances such as two or more of the suitable phase change materials discussed above. By selecting two or more different substances and forming a mixture thereof, transition temperatures can be adjusted over a wide range for any desired application. In some aspects of the present invention, a phase change material may include a copolymer of two or more substances such as two or more of the suitable phase change materials discussed above.

Phase change materials of the present invention may include phase change materials in a non-encapsulated form and phase change materials in an encapsulated form. A phase change material in a non-encapsulated form may be provided as a solid in a variety of forms (e.g., bulk form, powders, pellets, granules, flakes, and so forth) or as a liquid in a variety of forms (e.g., molten form, dissolved in a solvent, and so forth).

The percentage of PCM components in the cooling composition may vary depending on the desired application of the cooling composition. As an example, the cooling composition may include about 1% to about 50% PCM components. In other aspects, the cooling compositions may include about 1% to about 40%, about 10% to 50%, about 10% to 40%, about 15% to about 40%, about 10% to 35%, and about 15% to 35% PCM components. Therefore, while the ingredients in the cooling compositions may typically include about 1% to about 50% PCM components, some variability in the types of PCM components employed within the cooling compositions is acceptable so long as the cooling compositions provide sufficient immediate and long term cooling of the skin.

The cooling composition of the present invention is made by adding to a base formulation a neurosensory component, such as menthol, menthol derivatives, or an encapsulated cooling agent such as SALCOOL cooling composition from Salvona Technologies of New Jersey, U.S. The cooling composition produces a perception of an immediate and/or long term cooling sensation on skin when the neurosensory component is applied to skin.

Suitable neurosensory components for use herein include all neurosensory components for which the cooling sensation is a physiological or neurosensory effect due to the direct action of these agents on the nerve endings of the mammal body responsible for the detection of hot or cold with no or a limited occurrence of actual temperature change on the surface of the mammal body. It is believed that these agents act as a direct stimulus on the cold receptors at the nerve endings, which in turn stimulate the central nervous system. In this way a cooling sensation is simulated in the absence of real change in skin temperature. Due to the persistence of the stimulus, a long lasting cooling sensation is delivered even after removal of the cooling agent.

The cooling sensation may be personal to a given individual. Skin tests can be somewhat subjective, and some individuals experience a greater or lesser cooling sensation than others when subjected to the same test. The perception of a cooling sensation depends on the density of thermo-receptors on the skin and on the thickness of the skin. Subjects with thinner skin typically perceive a more intense cooling sensation. Without being bound by any particular theory, it is believed that the thinner the skin is, the more rapid is the penetration of the cooling agent through the skin and the greater is the absorption level thereof. Other factors such as geographic and racial factors may influence perception of a cooling sensation.

Without being bound by any particular theory, it is speculated that neurosensory components are able to penetrate through the skin surface and depolarize (clear the potential differential between the inside and outside nervous cell membranes by blocking calcium ion exchange) the membrane of cold receptors. The cold perception is the result of the depolarization.

More particularly, it is believed that due to the calcium-binding properties of neurosensory components, the equilibrium between the concentration of calcium ion outside and inside the nerve cell membrane is disturbed. By reducing the calcium ion level outside the nerve cell membrane, the membrane is depolarized, resulting in an increased discharge rate of nerve fibers and hence transfer of electrical stimuli to the central nervous system.

In addition, it is believed that the long lasting effect is linked to binding stability properties of the neurosensory component and the calcium ion complex. Greater stability of the complex neurosensory component-calcium ion yields a longer-duration link between the calcium and the neurosensory component, which leads to a longer-duration cooling sensation.

Studies performed on neurosensory component activity demonstrated that four features of the molecular structure of the neurosensory components are particularly important to deliver a cooling sensation. See H. R. Watson et al., Journal of the Society of Cosmetic Chemist, Vol. 29, p 185-200, 1978.

Suitable neurosensory components of the present invention may exhibit the following properties. 1) A hydrogen binding function—Neurosensory components appear to need an atom or group able to bind hydrogen. Stronger hydrogen binding capacities yield a stronger cooling sensation. 2) A compact hydrocarbon skeleton such that the body's thermo-receptors are able to recognize them. 3) A balance between their hydrophilic and hydrophobic parts for both delivering cooling properties and to enable them to penetrate the outer skin layers. 4) Typically a molecular weight of between 150 and 350.

Suitable neurosensory components of the present invention include menthol, menthol derivatives, an encapsulated cooling agent such as SALCOOL cooling composition from Salvona Technologies of New Jersey, U.S., menthyl lactate, menthyl salicylate, menthyl acetate, menthyl PCA, menthyl carbinol, methyl linalool, isoeugenol, methyl eugenol, ICE 1500 cooling sensate available from Qaroma, Baytown, Tex., menthone glycerol ketal, menthoxypropane-1,2-diol, (−)-isopulegol, cubebol, N-substituted p-menthane carboxamides, icilin, mint, mint oils, cucumber, chamomile, aloe, comfrey, anise, sage, carboamides, ketals, carboxamides, cyclohexanol derivatives, and/or cyclohexyl derivatives. Additional suitable neurosensory components are described in an article by John C. Leffingwell, Ph.D. at www.leffingwell.com/cooler_than_menthol.htm, which is hereby incorporated herein by reference to the extent it is consistent (i.e., not in conflict) herewith.

The percentage of neurosensory components in the cooling composition may vary depending on the desired application of the cooling composition. As an example, the cooling composition may include about 0.1% to about 5% neurosensory components. In other aspects, the cooling compositions may include about 0.5% to about 5%, about 1% to about 4%, about 1% to about 3%, or about 1% to about 2% neurosensory components. Therefore, while the ingredients in the cooling compositions may typically include about 0.1% to about 5% neurosensory components, some variability in the types of neurosensory components employed within the cooling compositions is acceptable so long as the cooling compositions provide sufficient immediate and long term cooling of the skin.

The cooling composition may further include an evaporative cooling component such as water or alcohol that provides the cooling composition with some of the short and long term cooling of the skin through the latent heat of evaporation from the alcohol (shorter term cooling) and water (longer term cooling). In some aspects, the water may be purified or distilled. In addition, the alcohol may be isopropyl alcohol, ethyl alcohol, or any other suitable alcohol.

Suitable evaporative cooling components of the present invention include water; hydrocarbons such as isododecane and isoeicosane; short chain alcohols such as ethanol and n-propanol; small branched chain alcohols such as isopropyl alcohol; fluorinated hydrocarbons such as perfluorodecalin, perfluoroheptane, perfluorohexane, and perfluoromethylcyclohexane; fluorinated alcohols such as C6-C12 perfluoroalkylethanol and perfluorocyclohexylmethanol; fluorinated ethers such as ethyl perfluorobutyl ether, ethyl perfluoroisobutyl ether, methyl perfluorobutyl ether, methyl perfluoroisobutyl ether, and perfluorohexylethyl dimethylbutyl ether; low molecular weight grades of dimethicone, particularly DOW CORNING 200 dimethicone fluid 5 cst; volatile cyclomethicones such as octamethyl cyclotetrasiloxane, decamethyl cyclopentasiloxane, dodecamethyl cyclohexasiloxane, and tetradecamethyl cycloheptasiloxane.

The percentage of water and alcohol in the cooling composition may vary depending on the desired application of the cooling composition. As an example, the cooling composition may include about 5% to about 95% water. In other aspects, the cooling composition may include about 10% to about 90% water. In other aspects, the cooling composition may include about 20% to about 85% water. In other aspects, the cooling composition may include about 30% to about 80%, about 40% to about 70%, about 50% to about 60%, or about 60% to about 70% water. In addition, the cooling composition may include about 5% to about 75% alcohol. In other aspects, the cooling composition may include about 15% to about 65%, about 25% to about 55%, about 35% to about 45%, or about 20% to about 40% alcohol.

The cooling composition may optionally include a surfactant that may promote emulsifying activity. Surfactants have the ability to lower the surface tension of water to reduce the interfacial tension between two immiscible substances. In some aspects, the surfactants in the cooling composition may enhance cleaning or removal of dirt, sweat, and/or sebum from the skin. Some surfactants may also act as a wetting agent to facilitate placing the cooling composition on a substrate (e.g., a wipe). In addition, some surfactants may act as emulsifying agents or solubilizing agents to emulsify or solubilize hydrophobic materials into hydro-alcohol formulations. Some variability in the types of surfactant employed within the cooling composition is acceptable so long as the surfactant provides sufficient emulsifying activity.

It should be noted that to achieve solubilization or emulsification of a lipophilic ingredient, the lipophilic ingredient (e.g., an oil soluble skin health benefit agent) must be compatible with a surfactant that is part of the cooling composition in order to obtain a stable formulation. As examples, surfactants may be selected from groups of sorbitan fatty acids (sorbitan monopalmitate, sorbitan monolaurate and the like), polyoxyethylene sorbitan fatty acid esters (polyoxyethylene 20 sorbitan monolaurate, polyoxyethylene sorbitan 20 monostearate, polyoxyethylene 4 sorbitan monostearate and the like), polyoxyethylene acids (polyoxyethylene 8 stearate, polyoxyethylene 20 stearate, and the like), and polyoxyethylene alcohols (polyoxyethylene 4 lauryl ether, polyoxyethylene 10 cetyl ether, polyoxyethylene 10 stearyl ether, polyoxyethylene 5.5 decyl ether, and the like), but the surfactant(s) can be selected from any suitable surfactants.

The cooling composition may include other active or inactive additives depending on the desired application of the cooling composition. It should be noted that the absolute weight of any additive to the cooling composition may vary.

In some aspects, the cooling composition may include therapeutic additives. Some example therapeutic additives include anti-microbial agents, pain relievers, anti-inflammatory agents, skin-protectants, antiseptics, sunscreens, insect repellents, exfoliants, deodorants, antiperspirants, vitamins (e.g., vitamin B, C or E), and aloe vera (among others).

The cooling composition may also include an additive that regulates the release of one or more of the items which form the cooling composition at a desired rate. As an example, the additive may provide for long term delivery of one or more items in the cooling composition thus increasing the useful life of a product that includes the cooling composition. The appropriate amount of such an additive will depend on the desired rate and duration of the release. Examples of such additives include water insoluble polymers such as ethylcellulose, acrylic resins, co-polymer of methacrylic acid and acrylic acid ethyl ester, polylactic acid, PLGA, polyurethane, polyethylene vinyl acetate copolymer, and polystyrene-butadiene copolymer (or mixtures thereof).

Other additives may be included in the cooling composition to facilitate delivering the cooling composition to skin. Some examples of such additives include lubricants, plasticizing agents, preservatives, thickeners, emulsion stabilizers, stick formers, suppository formers, film formers, cream formers, coatings, binders, carrier, coloring agents, moisturizers, chelating agents, fragrance and/or odor controlling agents, humectants, viscosity controlling agents, and pH-adjusting agents (among others).

It should be noted that any number and type of additives may be included in the cooling composition. Some of the other example additives include potassium lactate, vitamin E, vitamin C, fragrance, botanicals, citric acid, sodium hydroxide, and/or potassium chloride (among others).

The cooling composition may be administered directly to the skin for prophylactic, therapeutic, and/or hygienic use. The cooling composition may be administered in a single dose, in multiple doses, and/or in a continuous or intermittent manner depending on a variety of factors (e.g., the recipient's physiological condition).

The cooling composition may be formulated into a variety of articles (e.g., patches, bandages, sponges, wipes, and dressings). In addition, the viscosity of the cooling composition may be controlled in part by adding other items to the cooling composition.

The cooling composition may be administered in the form of a stick, powder/talc or other solid, solution, liquid, spray, bioadhesive gel, aerosol, foam, cream, gel, lotion, paste, jellies, or sprays. As an example, creams may be formulated with an aqueous or oily base with additional suitable thickening and/or gelling agents. In addition, lotions may be formulated with additional stabilizing agents, dispersing agents, suspending agents, thickening agents, or coloring agents.

In some aspects, the cooling composition may degrade slowly and remain attached to the skin for a period of time. As an example, the cooling composition may include a bioadhesive that has a cross-linking agent which is present to facilitate adhering the cooling composition to the skin. The bioadhesive may be included at various concentrations within the cooling composition in order to provide more or less adhesion to the skin.

When the cooling composition is a liquid, the cooling composition may be administered from absorbent materials (e.g., a bandage or sponge). The cooling composition may also be administered as a spray/aerosol that is applied to the skin using a pump-type or aerosol sprayer. In some aspects, the cooling composition may be provided in the form of a solution that is initially in the form of a concentrated liquid, dissolvable powder, or tablet where water, saline, or other liquid is added to form the cooling composition prior to use. The cooling composition may also be administered using an applicator (e.g., a squeeze-type or plunger-type applicator).

In various aspects of the present invention, the applications for the cooling compositions are many and varied. Broadly speaking, the cooling compositions can be classified as topical compositions, this term being taken in its broadest possible sense. Topical compositions include not only compositions such as perfumes, powders and other toiletries, lotions, liniments, oils and ointments applied to the external surfaces of the human body, whether for medical or other reasons, but also compositions applied to, or which, in normal usage, come in contact with internal mucous membranes of the body, such as those of the nose, mouth, or throat, whether by direct or indirect application or inhalation, and thus include nasal and throat sprays, dentifrice, mouthwash, and gargle compositions. Also included within the present invention are toilet hygienic articles such as cleansing tissues, wipes, toilet papers, diapers, sanitary napkins, panty liners, and the like, and toothpicks impregnated or coated with the compositions according to the present invention.

In a broad aspect of the invention, the composition is applied on an article suitable to be contacted or even worn in direct contact with human body. Such articles include hygienic articles for use by babies, men, and women, such as hygienic disposable absorbent articles.

Toiletries include after shave lotions, shaving soaps, creams and foams, toilet water, deodorants and antiperspirants, solid colognes, toilet soaps, bath oils and salts, shampoos, hair oils, talcum powders, face creams, hand creams, sunburn lotions, cleansing tissues, hygienic articles, dentifrices, toothpicks, mouthwashes, hair tonics, and eye drops. Topical pharmaceuticals including antiseptic ointments, liniments, lotions, decongestants, counter-irritants, cough mixtures, throat lozenges, and analgesics.

Because of their cooling sensation on the skin and on the mucous membranes of the mouth, throat, and nose, the cooling compositions of the present invention may be used in a variety of topical pharmaceutical compositions, particularly where a counter-irritant is required. Miscellaneous compositions include water-soluble adhesive compositions for envelopes, postage stamps, adhesive labels, etc.

Various aspects of the present invention may be directed to hygienic disposable articles such as bandages, thermal pads, acne pads, cold pads, wrist coolers, compresses, surgical pads/wound dressings, protective bedding covers, protective clothing, gloves, socks, pillow covers, protective face masks, ornamental and/or fashionable articles or eye wear, prostheses, plasters, wraps, hearing aids, and the like; hygienic disposable articles for absorbing perspiration such as perspiration pads, underarm sweat pads, shoe insoles, shirt inserts, sporting clothes, cap inside liners, and the like; and hygienic disposable absorbent articles for use by babies and adults such as panty liners, feminine napkins, incontinent pads, diapers, tampons, interlabial pads, dry or wet wipes, breast pads, human waste management devices, and the like.

EXAMPLE 1

Example 1 provides a cooling composition with a phase change material and a neurosensory component. This example demonstrates a cooling composition that provides short and long term skin cooling using a cooling lotion made with a phase change material and a neurosensory component.

A shea butter lotion formulation was modified to add 10% LURAPRET 28 phase change powder and 5% SALCOOL 4653 cooling composition as described in this example. 132.56 g DI water, 0.41 g CARBOPOL 980 thickener, 11.36 g glycerin, and 0.10 g VERSENE 100xl chelating agent were combined and heated to 70 C. Phase B (1.62 g GENEROL 122NPRL phytosterol, 2.52 g stearyl alcohol, 1.55 g cetyl alcohol, 1.5 g stearic acid, 2.01 g CERAPHYL 424 emollient, 4.09 g ARLACEL 165 emulsifier, 0.5 g synthetic beeswax, 0.53 g LIPEX 102 surfactant, 0.08 g BHT, 6.02 g sunflower oil, 2.02 g FINSOLV TN emollient, 2.01 g DC 200 dimethicone (100 cst), and 20.01 g LURAPRET 28 phase change powder) was combined and heated separately until all the components melted. Note—the LURAPRET 28 phase change powder did not melt. Phase B was combined with phase A with stirring, the pH was adjusted to 5.5 with 10% KOH, and the resultant formulation weighed to check and adjust for water loss. The formulation was then homogenized. It was allowed to cool with stirring. At 50 C, phase C (2.03 g PARAGON MEPB preservative, 10.47 g SALCOOL 4653 cooling compound) was added to the formulation. The cooling composition that was created in the lab was tested by lab personnel and provided a cooling sensation for 10-30 minutes, depending on the individual.

EXAMPLE 2

Example 2 provides a cooling composition with multiple phase change materials and neurosensory components. This example demonstrates a cooling composition that provides short and long term skin cooling by using a combination of melting points in the phase change material plus at least two neurosensory components.

15 g safflower oil, 2 g MAGNASPERSE thickener, and 10 g FINSOLV TN emollient were combined and allowed to stir for one hour. 15 g petrolatum, 2 g AEROSIL 300 silica filler, and 1 g cetearyl alcohol were then added. The combination was heated to 55° C. to melt the cetearyl alcohol, then heating was discontinued. 10 g ABIL Care 85 emulsifier, 15 g SIL-SOFT ETS trisiloxane, and 15 g DC 200 dimethicone fluid (0.65 cst) were added to the combination. The combination was homogenized for 3-5 minutes and allowed to cool. When the formulation reached room temperature, 4 g FRESCOLAT Plus cooling agent, 2 g LURAPRET 18 phase change material, 2 g LURAPRET 28 phase change material, 2 g LURA-PRET 35 phase change material, 2 g SALCOOL cooling compound, and 3 g xylitol were added. The cooling composition that was created in the lab was tested by lab personnel and provided a cooling sensation for 10-30 minutes, depending on the individual.

These and other modifications and variations to the present invention may be practiced by those of ordinary skill in the art, without departing from the spirit and scope of the present invention, which is more particularly set forth in the appended claims. In addition, it should be understood that aspects of the various aspects of the present invention may be interchanged either in whole or in part. Furthermore, those of ordinary skill in the art will appreciate that the foregoing description is by way of example only, and is not intended to limit the invention so further described in such appended claims.

What is claimed:

1. A topical temperature change composition comprising effective amounts of:
   a neurosensory component;
   a first phase change component having a first phase change temperature between about 15 degrees C. and about 40 degrees C.; and
   a second phase change component having a second phase change temperature different from the first phase change temperature, wherein the second phase change temperature is between about 15 degrees C. and about 40 degrees C.

2. The composition of claim 1, wherein the first phase change component is one of a hydrocarbon, a wax, an oil, a fatty acid, a fatty acid ester, a dibasic acid, a dibasic ester, a 1-halide, a primary alcohol, an aromatic compound, an anhydride, ethylene carbonate, a polyhydric alcohol, and a polymer.

3. The composition of claim 1, wherein the first phase change component is an encapsulated paraffin wax.

4. The composition of claim 1, wherein the second phase change component is different from the first phase change component and is one of a hydrocarbon, a wax, an oil, a fatty acid, a fatty acid ester, a dibasic acid, a dibasic ester, a 1-halide, a primary alcohol, an aromatic compound, an anhydride, ethylene carbonate, a polyhydric alcohol, and a polymer.

5. The composition of claim 1, wherein the second phase change temperature is higher than the first phase change temperature.

6. The composition of claim 1, further comprising a third phase change component having a third phase change temperature different from the first and second phase change temperatures, wherein the third phase change temperature is between about 15 degrees C. and about 40 degrees C.

7. The composition of claim 6, wherein the third phase change temperature is higher than the second phase change temperature.

8. The composition of claim 1, wherein the neurosensory component is one of menthol, menthol derivatives, menthyl lactate, menthyl salicylate, menthyl acetate, menthyl PCA, menthyl carbinol, methyl linalool, isoeugenol, methyl eugenol, menthone glycerol ketal, menthoxypropane-1,2-diol, (−)-isopulegol, cubebol, N-substituted p-menthane carboxamides, icilin, mint, mint oils, cucumber, chamomile, aloe, comfrey, anise, sage, carboamides, ketals, carboxamides, cyclohexanol derivatives and/or cyclohexyl derivatives.

9. The composition of claim 1, wherein the neurosensory component is encapsulated.

10. The composition of claim 1, further comprising an evaporative cooling component, wherein the evaporative cooling component is one of a hydrocarbon, a short chain alcohol, a small branched chain alcohol, a fluorinated hydrocarbon, a fluorinated alcohol, a fluorinated ether, a low molecular weight grade of dimethicone, and a volatile cyclomethicone.

11. The composition of claim 1, wherein the first phase change temperature is between about 18 degrees C. and about 35 degrees C.

12. The composition of claim 1, wherein the temperature change composition is adapted to be applied with an applicator.

13. The composition of claim 12, wherein the applicator is a disposable absorbent article.

14. The composition of claim 12, wherein the applicator is a wipe.

15. A topical temperature change composition comprising effective amounts of:
  an evaporative cooling component, wherein the evaporative cooling component is one of a hydrocarbon, a short chain alcohol, a small branched chain alcohol, a fluorinated hydrocarbon, a fluorinated alcohol, a fluorinated ether, a low molecular weight grade of dimethicone, and a volatile cyclomethicone;
  a first phase change component having a first phase change temperature between about 15 degrees C. and about 40 degrees C.; and
  a second phase change component having a second phase change temperature different from the first phase change temperature, wherein the second phase change temperature is between about 15 degrees C. and about 40 degrees C.

16. The composition of claim 15, wherein the first phase change component is an encapsulated paraffin wax.

17. The composition of claim 15, wherein the second phase change temperature is higher than the first phase change temperature.

18. The composition of claim 15, further comprising a third phase change component having a third phase change temperature different from the first and second phase change temperatures, wherein the third phase change temperature is between about 15 degrees C. and about 40 degrees C.

19. The composition of claim 18, wherein the third phase change temperature is higher than the second phase change temperature.

20. The composition of claim 19, wherein the first, second, and third phase change components are each one of a hydrocarbon, a wax, an oil, a fatty acid, a fatty acid ester, a dibasic acid, a dibasic ester, a 1-halide, a primary alcohol, an aromatic compound, an anhydride, ethylene carbonate, a polyhydric alcohol, and a polymer.

21. The composition of claim 15, further comprising a neurosensory component, wherein the neurosensory component is one of menthol, menthol derivatives, menthyl lactate, menthyl salicylate, menthyl acetate, menthyl PCA, menthyl carbinol, methyl linalool, isoeugenol, methyl eugenol, menthone glycerol ketal, menthoxypropane-1,2-diol, (−)-isopulegol, cubebol, N-substituted p-menthane carboxamides, icilin, mint, mint oils, cucumber, chamomile, aloe, comfrey, anise, sage, carboamides, ketals, carboxamides, cyclohexanol derivatives and/or cyclohexyl derivatives.

22. A topical temperature change composition for cooling skin, the composition comprising effective amounts of:
  a neurosensory component, wherein the neurosensory component is one of menthol, menthol derivatives, menthyl lactate, menthyl salicylate, menthyl acetate, menthyl PCA, menthyl carbinol, methyl linalool, isoeugenol, methyl eugenol, menthone glycerol ketal, menthoxypropane-1,2-diol, (−)-isopulegol, cubebol, N-substituted p-menthane carboxamides, icilin, mint, mint oils, cucumber, chamomile, aloe, comfrey, anise, sage, carboamides, ketals, carboxamides, cyclohexanol derivatives and/or cyclohexyl derivatives;
  a first phase change component having a first phase change temperature between about 15 degrees C. and about 40 degrees C.; and
  a second phase change component having a second phase change temperature different from the first phase change temperature, wherein the second phase change temperature is between about 15 degrees C. and about 40 degrees C.

23. The composition of claim 22, wherein each of the first phase change component and the second phase change component is one of a hydrocarbon, a wax, an oil, a fatty acid, a fatty acid ester, a dibasic acid, a dibasic ester, a 1-halide, a primary alcohol, an aromatic compound, an anhydride, ethylene carbonate, a polyhydric alcohol, and a polymer.

24. The composition of claim 22, wherein one of the first phase change component and the second phase change component is an encapsulated paraffin wax.

25. The composition of claim 22, further comprising a third phase change component having a third phase change temperature different from both the first and second phase change temperatures, wherein the third phase change temperature is between about 15 degrees C. and about 40 degrees C.

26. The composition of claim 22, further comprising an evaporative cooling component, wherein the evaporative cooling component is one of a hydrocarbon, a short chain alcohol, a small branched chain alcohol, a fluorinated hydrocarbon, a fluorinated alcohol, a fluorinated ether, a low molecular weight grade of dimethicone, and a volatile cyclomethicone.

27. A topical temperature change composition comprising effective amounts of:
  a neurosensory component;
  an evaporative cooling component, wherein the evaporative cooling component is one of a hydrocarbon, a short chain alcohol, a small branched chain alcohol, a fluorinated hydrocarbon, a fluorinated alcohol, a fluorinated ether, a low molecular weight grade of dimethicone, and a volatile cyclomethicone;
  a first phase change component having a first phase change temperature between about 15 degrees C. and about 40 degrees C.; and
  a second phase change component having a second phase change temperature different from the first phase change temperature, wherein the second phase change temperature is between about 15 degrees C. and about 40 degrees C.

28. The composition of claim 27, wherein the first and second phase change components are each one of a hydrocarbon, a wax, an oil, a fatty acid, a fatty acid ester, a dibasic acid, a dibasic ester, a 1-halide, a primary alcohol, an aromatic compound, an anhydride, ethylene carbonate, a polyhydric alcohol, and a polymer.

29. The composition of claim 27, wherein the neurosensory component is one of menthol, menthol derivatives, menthyl lactate, menthyl salicylate, menthyl acetate, menthyl PCA, menthyl carbinol, methyl linalool, isoeugenol, methyl eugenol, menthone glycerol ketal, menthoxypropane-1,2-diol, (−)-isopulegol, cubebol, N-substituted p-menthane carboxamides, icilin, mint, mint oils, cucumber, chamomile, aloe, comfrey, anise, sage, carboamides, ketals, carboxamides, cyclohexanol derivatives and/or cyclohexyl derivatives.

* * * * *